United States Patent
Lee et al.

(10) Patent No.: US 9,616,463 B2
(45) Date of Patent: Apr. 11, 2017

(54) PROBE FOR ULTRASOUND SYSTEM AND METHOD OF MANUFACTURING THE SAME

(75) Inventors: Sung Jae Lee, Seoul (KR); Jung Lim Park, Seoul (KR); Jae Yk Kim, Seoul (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 566 days.

(21) Appl. No.: 12/621,328

(22) Filed: Nov. 18, 2009

(65) Prior Publication Data

US 2010/0125209 A1    May 20, 2010

(30) Foreign Application Priority Data

Nov. 19, 2008    (KR) .................. 10-2008-0115409

(51) Int. Cl.
*A61B 8/00* (2006.01)
*B06B 1/06* (2006.01)
*A61B 8/08* (2006.01)

(52) U.S. Cl.
CPC .............. *B06B 1/0629* (2013.01); *A61B 8/08* (2013.01); *A61B 8/44* (2013.01); *A61B 8/4483* (2013.01); *H01L 2924/0002* (2013.01); *Y10T 29/49005* (2015.01)

(58) Field of Classification Search
CPC   A01N 43/80; A01N 43/90; H01L 2924/0002; H01L 2924/00; B06B 1/0629; A61B 8/44; A61B 8/08; A61B 8/00; A61B 8/4483; A61B 8/4281; G01S 7/52079
USPC ......................................... 600/459
See application file for complete search history.

(56) References Cited

U.S. PATENT DOCUMENTS

| | | | |
|---|---|---|---|
| 5,810,009 A  * | 9/1998 | Mine ..................... B06B 1/0622 |
| | | | 310/334 |
| 6,104,126 A  * | 8/2000 | Gilmore ....................... 310/334 |
| 6,308,389 B1 * | 10/2001 | Tezuka ......................... 29/25.35 |
| 2003/0127947 A1* | 7/2003 | Chandran et al. ............ 310/328 |
| 2006/0184033 A1* | 8/2006 | Cerofolini ................ A61B 8/00 |
| | | | 600/459 |

FOREIGN PATENT DOCUMENTS

| | | | |
|---|---|---|---|
| JP | 05-227594 A | 9/1993 |
| JP | 2005-125071 A | 5/2005 |

* cited by examiner

*Primary Examiner* — Joel Lamprecht
(74) *Attorney, Agent, or Firm* — McDermott Will & Emery LLP

(57) ABSTRACT

A probe for an ultrasound system, and a method of manufacturing the same are disclosed. The probe includes a backing layer, an electrode part formed on the backing layer, and a piezoelectric member installed to the electrode part. The probe is manufactured by connecting the piezoelectric member to the PCB via a unidirectional conduction part, instead of soldering which requires difficult and laborious operations, thereby allowing easy connection therebetween while reducing an operation time for connection.

19 Claims, 6 Drawing Sheets

PROBE FOR ULTRASOUND SYSTEM AND METHOD OF MANUFACTURING THE SAME

CROSS-REFERENCE TO RELATED APPLICATION

The present application claims the benefit of Korean Patent Application No. 10-2008-0115409 filed on Nov. 19, 2008, the entire contents of which are incorporated herein by reference.

BACKGROUND OF THE INVENTION

1. Field of the Invention

The present invention relates to a probe and, more particularly, to a probe for an ultrasound system that generates internal images of a patient body with ultrasound waves, and a method of manufacturing the same.

2. Description of the Related Art

Generally, an ultrasound system refers to a non-invasive apparatus that irradiates an ultrasound signal from a surface of a patient body towards a target internal organ beneath the body surface and obtains an image of a monolayer or blood flow in soft tissue from information in the reflected ultrasound signal (ultrasound echo-signal). The ultrasound system has been widely used for diagnosis of the heart, the abdomen, the urinary organs, and in obstetrics and gynecology due to various merits such as small size, low price, real-time image display, and high stability through elimination of any radiation exposure, as compared with other image diagnostic systems, such as X-ray diagnostic systems, computerized tomography scanners (CT scanners), magnetic resonance imagers (MRIs), nuclear medicine diagnostic apparatuses, and the like.

Particularly, the ultrasound system includes a probe which transmits an ultrasound signal to a patient body and receives the ultrasound echo-signal reflected therefrom to obtain the ultrasound image of the patient body.

The probe includes a transducer, a case with an open upper end, a cover coupled to the open upper end of the case to directly contact the body surface of the patient, and the like.

The transducer includes a piezoelectric layer in which a piezoelectric material converts electrical signals into sound signals or vice versa while vibrating, a coordination layer reducing a difference in sound impedance between the piezoelectric layer and a patient body to allow as much of the ultrasound waves generated from the piezoelectric layer to be transferred to the patient body as possible, a lens layer focusing the ultrasound waves, which travel in front of the piezoelectric layer, onto a predetermined point, and a backing layer blocking the ultrasound waves from traveling in a rearward direction of the piezoelectric layer to prevent image distortion.

The piezoelectric layer includes a piezoelectric member and electrodes provided to upper and lower ends of the piezoelectric member, respectively. Further, a printed circuit board (PCB) is bonded to the piezoelectric layer. The PCB is joined to the piezoelectric member by soldering with a solder such as lead or the like.

Here, since soldering between the piezoelectric member and the PCB is a difficult and laborious operation entailing heat generation, not only does the probe require a long manufacturing time, but also is likely to undergo deterioration in performance of the piezoelectric member resulting from the heat generated during the soldering operation. Moreover, since the soldering is carried out by a manual operation, a soldered portion has a low durability and uniformity, causing deterioration in performance of the probe. Therefore, there is a need for an improved probe that overcomes such problems.

SUMMARY OF THE INVENTION

The present invention is conceived to solve the problems of the conventional technique as described above, and an aspect of the present invention is to provide an improved probe for an ultrasound system, which permits easy manufacture while preventing performance deterioration resulting from heat generation or defective connection between a piezoelectric member and a PCB during manufacturing, and a method of manufacturing the same.

In accordance with an aspect of the present invention, a probe for an ultrasound system includes a backing layer; an electrode part formed on the backing layer; and a piezoelectric member installed to the electrode part.

The probe may further include a unidirectional conduction part installed to the electrode part.

The electrode part may include a plurality of electrode parts arranged side by side.

The unidirectional conduction part may include an anisotropic conduction material.

The probe may further include a printed circuit board (PCB) installed to the unidirectional conduction part.

The probe may further include first and second electrodes formed on the piezoelectric member.

The first and second electrodes may be formed symmetrically to each other.

Each of the first and second electrodes may be formed in a "J"-shape surrounding the piezoelectric member.

The electrode part may have shapes respectively corresponding to the first electrode and the second electrode so as to be bonded to the first and second electrodes.

The piezoelectric member may include a plurality of piezoelectric members arranged in an array.

In accordance with another aspect of the present invention, there is provided a method of manufacturing a probe for an ultrasound system, the probe including a backing layer, and a piezoelectric member having first and second electrodes, the method including: forming an electrode part on the backing layer; and installing the piezoelectric layer to the electrode part.

The method may further include patterning the electrode part.

The step of patterning the electrode part may be performed to divide the electrode part into a plurality of electrode parts separated from each other.

The method may further include installing a unidirectional conduction part to the electrode part, the electrode part comprising a plurality of electrode parts arranged side by side.

The method may further include installing a PCB to the unidirectional conduction part.

The first and second electrodes may be formed symmetrically to each other on the piezoelectric member.

The first and second electrodes may be formed in a "J"-shape surrounding the piezoelectric member.

The step of forming an electrode part on the backing layer may include forming the electrode part thereon after forming a reinforcement material on the backing layer, the reinforcement material enhancing a bonding force between the backing layer and the electrode part.

According to the embodiment of the present invention, the probe is manufactured by connecting the piezoelectric member to the PCB via the unidirectional conduction part, instead of soldering which requires difficult and laborious operations, thereby allowing easy connection therebetween while reducing an operation time for connection.

Further, since the PCB is connected to the piezoelectric member via the electrode part formed on the backing layer instead of being directly installed to the piezoelectric member, the PCB is not interposed between the backing layer and the piezoelectric member, thereby improving performance of the piezoelectric member while minimizing performance reduction thereof caused by heat generated during installation of the PCB.

Furthermore, the electrode parts separated from each other for each channel are firmly and uniformly connected to the line electrodes on the PCB via the unidirectional conduction part in a single heating and pressing operation instead of the laborious soldering operation, thereby preventing performance deterioration or malfunction of the probe resulting from low durability and non-uniformity of connection therebetween in the probe.

BRIEF DESCRIPTION OF THE DRAWINGS

The above and other aspects, features and advantages of the present invention will become apparent from the following description of exemplary embodiments given in conjunction with the accompanying drawings, in which.

DETAILED DESCRIPTION OF THE EMBODIMENT

Exemplary embodiments of the present invention will now be described in detail with reference to the accompanying drawings. It should be noted that the drawings are not to precise scale and may be exaggerated in thickness of lines or size of components for descriptive convenience and clarity only. Furthermore, terms used herein are defined by taking functions of the present invention into account and can be changed according to the custom or intention of users or operators. Therefore, definition of the terms should be made according to overall disclosures set forth herein.

Figure 1:
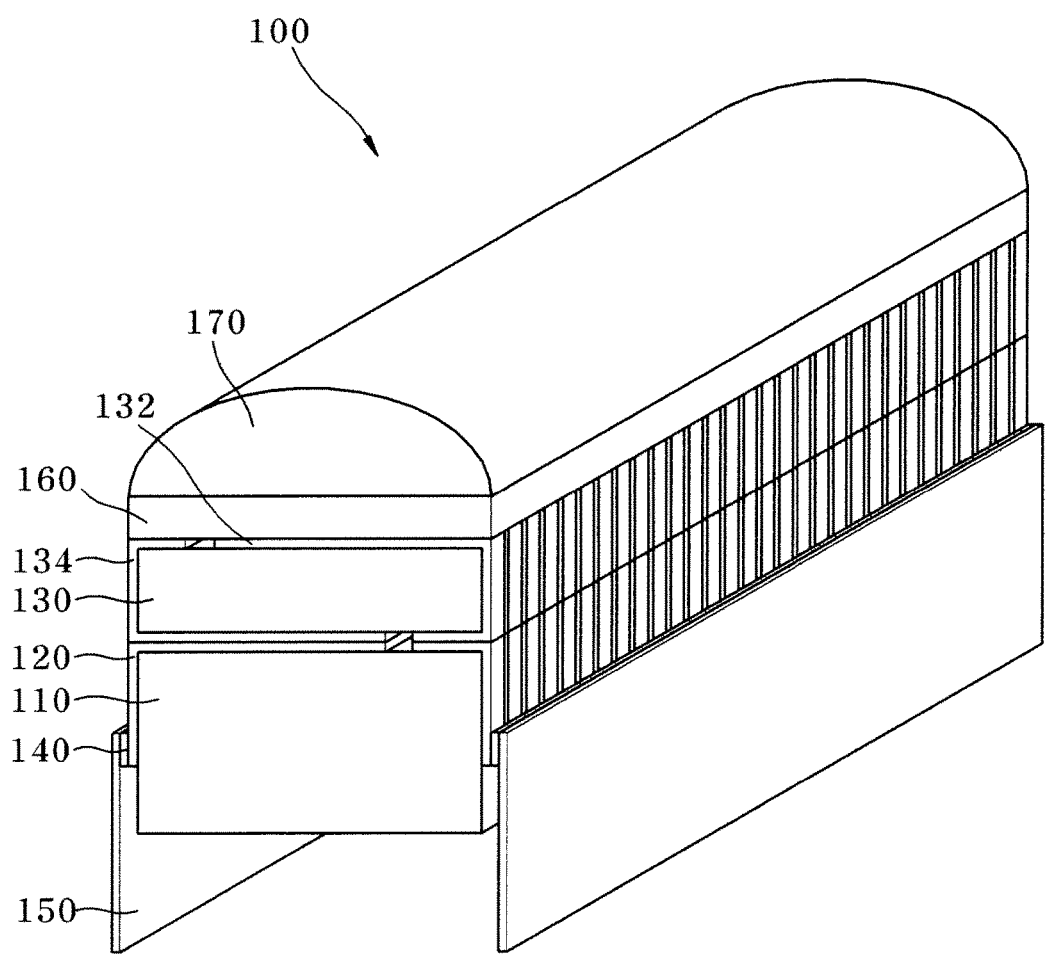
FIG. 1 is a perspective view of a probe for an ultrasound system according to an embodiment of the present invention.

Referring to FIG. 1, which is a perspective view of a probe 100 for an ultrasound system according to an embodiment of the present invention, the probe 100 includes a backing layer 110, an electrode part 120, and a piezoelectric member 130.

The backing layer 110 is disposed at the rear of the piezoelectric member 130. The backing layer 110 reduces a pulse width of an ultrasound wave by suppressing free vibration of the piezoelectric member 130, and prevents image distortion by blocking unnecessary propagation of the ultrasound wave in the rearward direction of the piezoelectric member 130. The backing layer 110 can be formed of a material containing a rubber to which epoxy, tungsten powder, and the like are added.

The electrode part 120 is formed on the backing layer 110 and is disposed between the backing layer 110 and the piezoelectric member 130. The electrode part 120 may be formed of a highly conductive material, such as gold, silver or copper, by deposition, sputtering, plating, spraying, or the like.

The piezoelectric member 130 is "installed" to the electrode part 120. The piezoelectric member 130 generates ultrasound waves using a resonance phenomenon. The piezoelectric member 130 may be formed of a ceramic of lead zirconate titanate (PZT), a PZNT single crystal made of a solid solution of lead zinc niobate and lead titanate, a PZMT single crystal made of a solid solution of lead magnesium niobate and lead titanate, or the like.

Herein, the term "installing" or "installed" means that two or more components are electrically connected to each other through interconnection therebetween. Hence, the piezoelectric member 130 is electrically connected to the electrode part 120 laminated on the backing layer 110 through interconnection with the electrode part 120, so that the piezoelectric member 130 can be installed to the electrode part 120.

For this purpose, the piezoelectric member 130 is formed with first and second electrodes 132 and 134. The first and second electrodes 132 and 134 are disposed to surround the piezoelectric member 130 and are electrically connected to the electrode part 120 through interconnection therewith. The first and second electrodes 132 and 134 may be formed of a highly conductive metal such as gold, silver or copper. Here, one of the first and second electrodes 132 and 134 serves as a positive pole of the piezoelectric member 130, and the other serves as a negative pole of the piezoelectric member 130. The first and second electrodes 132 and 134 are separated from each other to allow the positive pole and the negative pole to be separated from each other. In this embodiment, the first and second electrodes 132 and 134 are illustrated as serving as the positive and negative poles, respectively.

Further, the first and second electrodes 132 and 134 are configured to be disposed symmetrically to each other, thereby making upper and lower portions of the piezoelectric member 130 symmetrical to each other. Herein, each of the first and second electrodes 132 and 134 may have a "J"-shape that surrounds the piezoelectric member 130. With the first and second electrodes 132 and 134 disposed on the piezoelectric member 130, the upper and lower portions of the piezoelectric member 130 are symmetrical to each other, so that there is no need for differentiating the upper and lower portions of the piezoelectric member 130, thereby allowing the piezoelectric member 130 to be disposed on the electrode part 120 without differentiating the upper and lower portions thereof.

An array of piezoelectric members 130 with the configuration described above are arranged to form multiple channels. Hence, a plurality of electrode parts 120 may also be disposed side by side to constitute an array of electrode parts 120 corresponding to the array of piezoelectric members 130.

In this embodiment, the electrode part 120 is divided into the plural electrode parts 120 separated a predetermined distance from each other on a single backing layer 110 by dicing, and the plural electrode parts 120 are arranged side by side to constitute the array of electrode parts 120. However, the present invention is not limited to this configuration. Alternatively, both the electrode part 120 and the backing layer 110 may be divided into plural electrode parts 120 and plural backing layers 110 separated a predetermined distance from each other by dicing, such that plural laminates of the backing layers 110 and the electrode parts 120 may be disposed side by side in an array.

Further, each of the electrode parts 120 has shapes corresponding to the first and second electrodes 132 and 134 so as to be bonded to the first and second electrodes 132 and 134. That is, a portion of the electrode part 120 to be bonded to the first electrode 132 and a portion of the electrode part 120 to be bonded to the second electrode 134 are separated from each other and patterned to have shapes corresponding to the first electrode 132 and the second electrode 134, respectively.

The probe 100 for an ultrasound system according to this embodiment may further include a unidirectional conduction part 140 and PCBs 150.

The unidirectional conduction part 140 is installed to the electrode parts 120 which are disposed in an array as described above. A single unidirectional conduction part 140 comprising an anisotropic conduction material is installed to each side of the first and second electrodes 132 and 134.

The anisotropic conduction material is a bonding material which can accomplish electrical and mechanical coupling between electrodes by application of a predetermined pressure and heat thereto. The anisotropic conduction material has properties dependent on the application direction of pressure, so that only a part of the anisotropic conduction material exposed to pressure exhibits electrical conductivity, but other parts thereof free from the pressure do not exhibit the electrical conductivity. Thus, the unidirectional conduction part 140 comprising the anisotropic conduction material allows separation of electrodes between channels in a single mechanical process.

The PCBs 150 are installed to the unidirectional conduction part 140. The PCBs 150 are disposed substantially perpendicular with respect to the direction in which the backing layer 110 and the piezoelectric members 130 are laminated. The PCB 150 includes a flexible printed circuit board (FPCB), and any other configurations capable of supplying signals or electricity.

According to this embodiment, the PCB 150 having a plurality of line electrodes (not shown) formed thereon is disposed on each side of the first and second electrodes 132 and 134. The PCBs 150 are connected to the electrode parts 120 via the unidirectional conduction part 140.

In other words, when the PCBs 150 are compressed at a predetermined pressure and heat with the unidirectional conduction part 140 interposed therebetween, each of the PCBs 150 is mechanically coupled to the backing layer 110 via the unidirectional conduction part 140 while the plural line electrodes thereof are electrically connected to the electrode parts 120. A detailed description of this configuration will be described below.

Reference numerals 160 and 170 indicate a coordination layer of a glass or resin material for reducing a difference in sound impedance between a patient body and the probe, and a lens layer for focusing ultrasound waves traveling in front of the piezoelectric member 130 onto a particular point, respectively.

Figure 2:
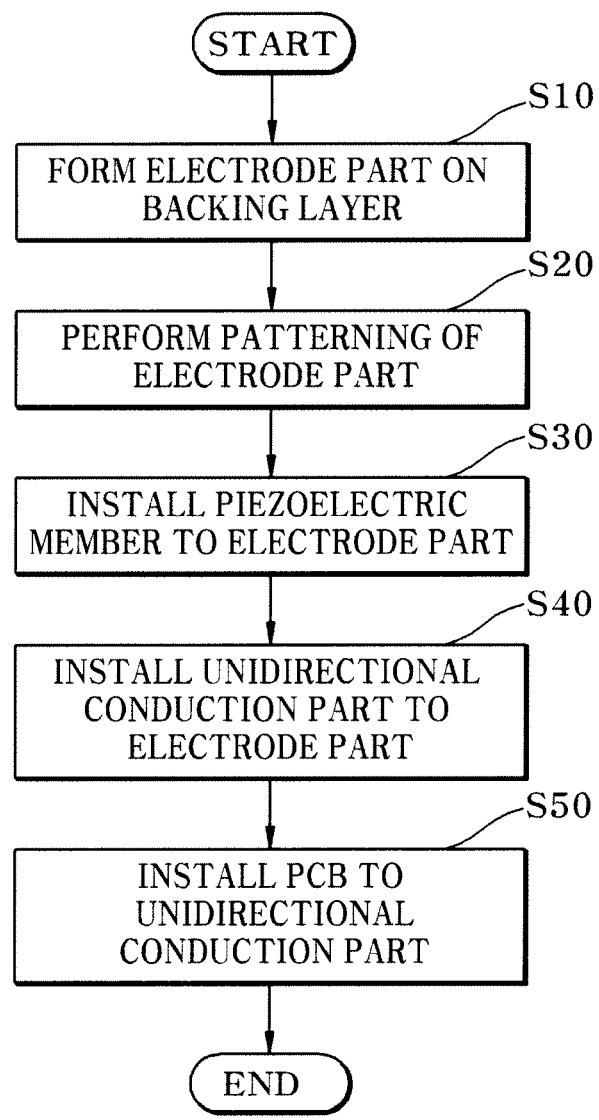
FIGS. 2 and 3 are flowcharts of a method of manufacturing a probe for an ultrasound system according to an embodiment of the present invention.
Figure 3:
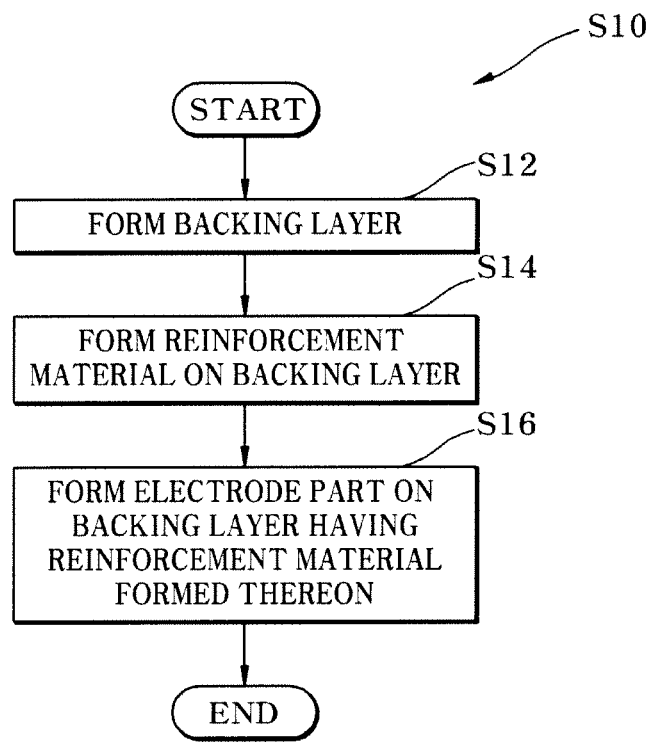
Figure 4:
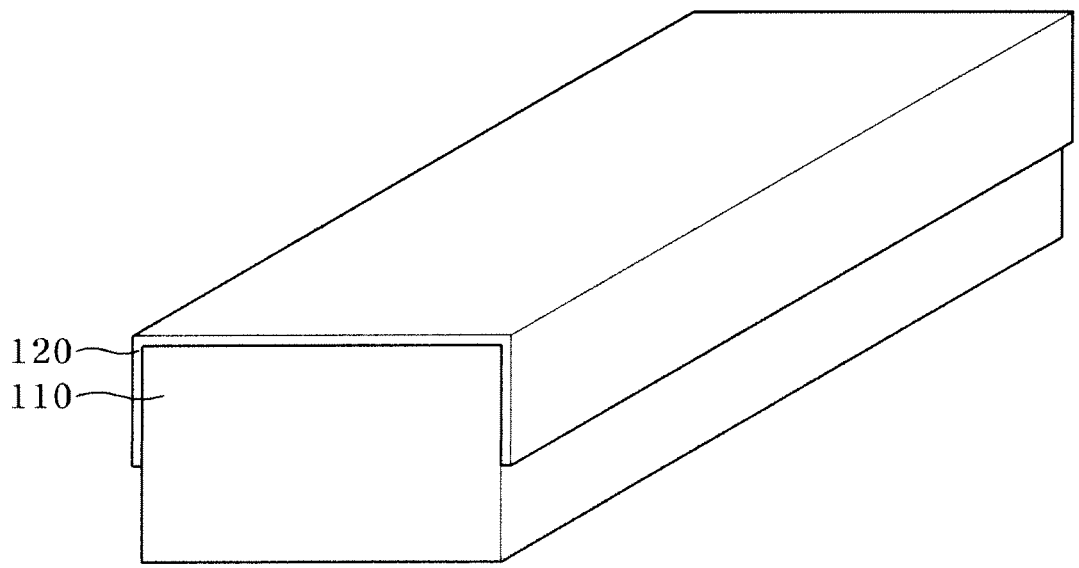
FIGS. 4 and 5 are views illustrating a process of forming an electrode part on a backing layer.
Figure 5:
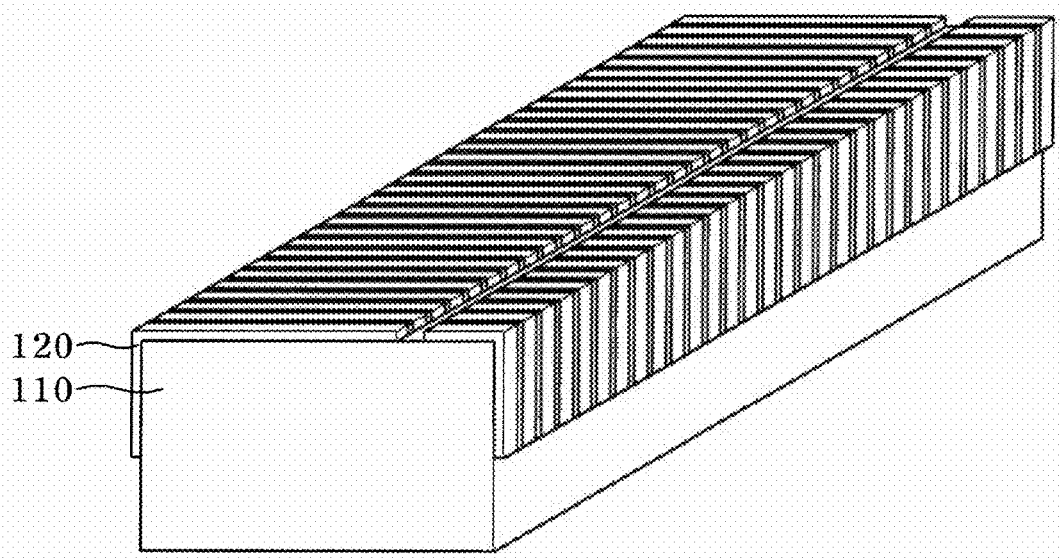
Figure 6:
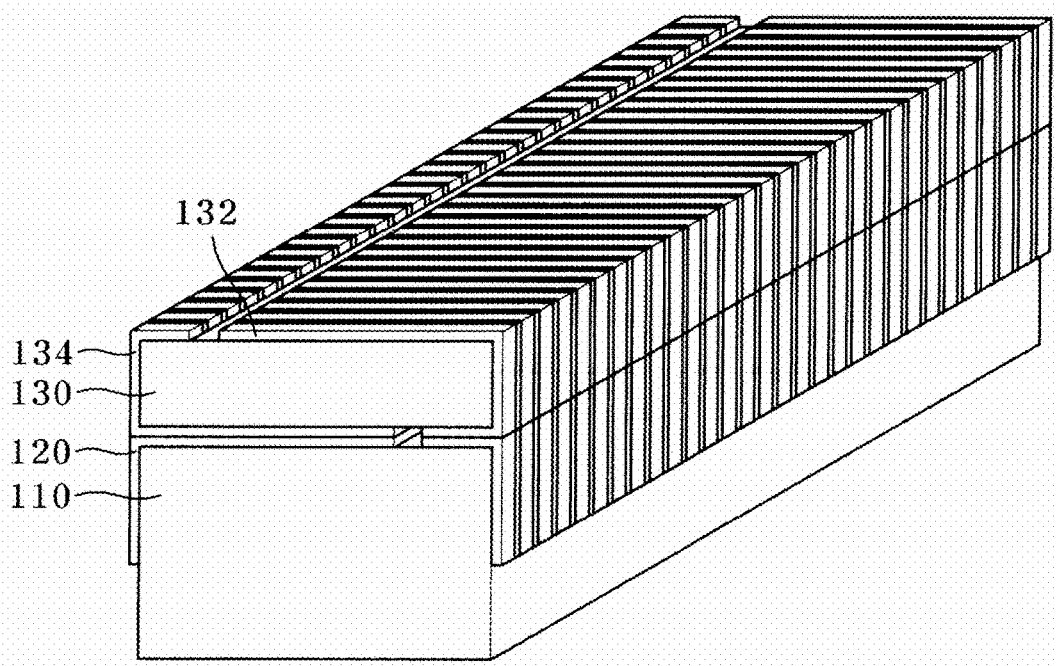
FIGS. 6 to 8 are views illustrating a process of installing PCBs to the electrode part.
Figure 7:
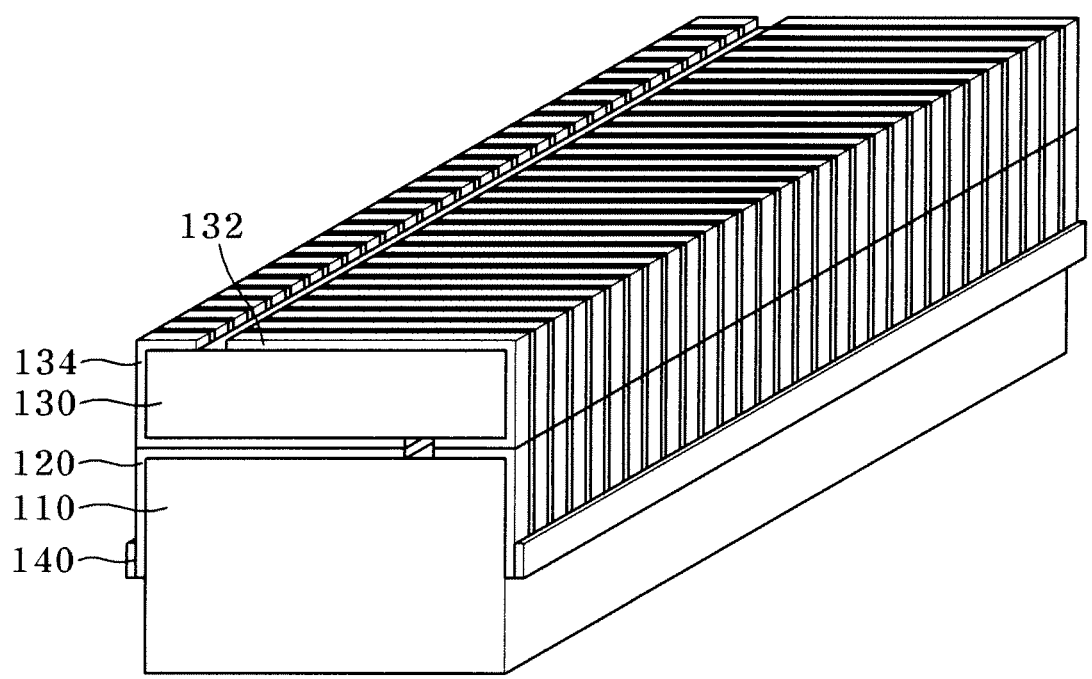
Figure 8:
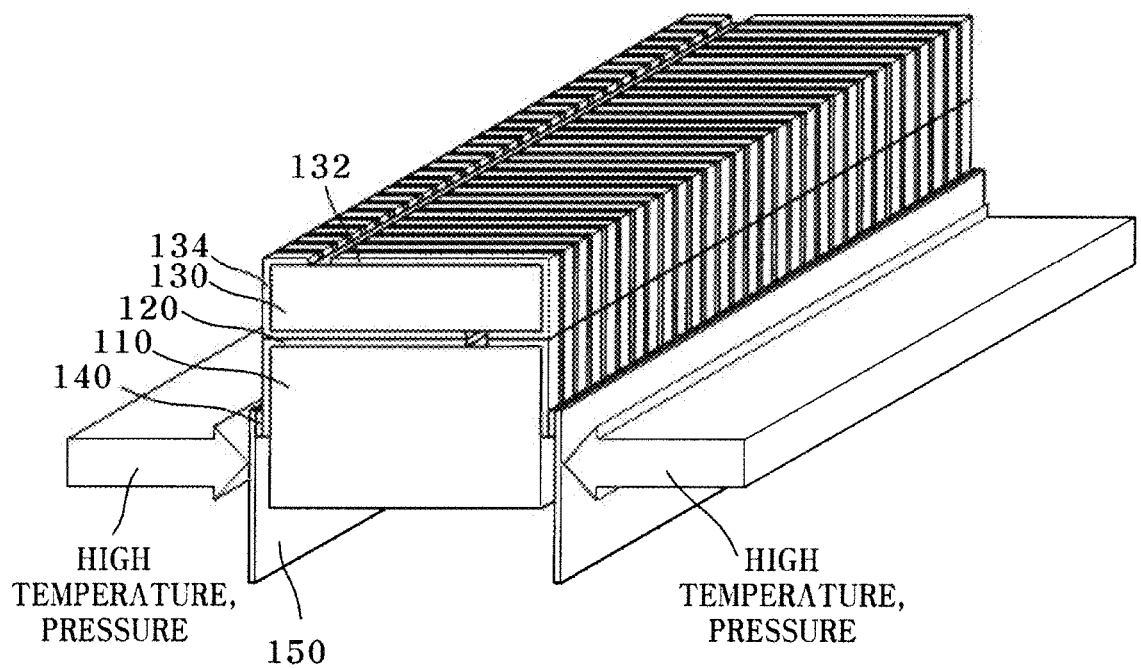

FIGS. 2 and 3 are flowcharts of a method of manufacturing a probe for an ultrasound system according to an embodiment of the present invention, FIGS. 4 and 5 are views illustrating a process of forming an electrode part on a backing layer, and FIGS. 6 to 8 are views illustrating a process of installing PCBs to the electrode part.

Referring to FIGS. 2 to 8, a method of manufacturing a probe for an ultrasound system according to an embodiment of the present invention will now be described.

To manufacture a probe 100 for an ultrasound system according to an embodiment of the invention, first, an electrode part 120 is formed on a backing layer 110 in S10.

To form the electrode part 120 on the backing layer 110, first, the backing layer 110 is formed using a material including a rubber, to which epoxy resin or tungsten powder is added, in S12, and a reinforcement material (not shown) is formed on the backing layer 110 to enhance a bonding force between the backing layer 110 and the electrode part 120, in S14. The reinforcement material may be composed of a material that comprises chrome, nickel, and the like. Then, in S16, the electrode part 120 is formed on the backing layer 110 where the reinforcement material is formed. The electrode part 120 may be formed of a highly conductive material, such as gold, silver or copper, by deposition, sputtering, plating, spraying, or the like.

Then, the electrode part 120 formed on the backing layer 110 is subjected to a patterning process in S20 as shown in FIG. 5. In this patterning process, the electrode part 120 is patterned to have shapes corresponding to first and second electrodes 132 and 134 so as to be bonded to the first and second electrodes 132 and 134. In other words, the electrode part 120 is patterned such that a portion of the electrode part 120 to be bonded to the first electrode 132 and a portion of the electrode part 120 to be bonded to the second electrode 134 are separated from each other. The electrode part 120 may be patterned by dicing, photolithographic patterning, etching, or the like.

Next, as shown in FIG. 6, a piezoelectric member 130 is installed to the electrode part 120 in S30. Here, the piezoelectric member 130 is electrically connected to the electrode part 120 laminated on the backing layer 110 through interconnection with the electrode part 120, so that the piezoelectric member 130 can be installed to the electrode part 120.

Since the first and second electrodes 132 and 134 are formed symmetrically to each other in a "J"-shape surrounding the piezoelectric member 130, the upper and lower portions of the piezoelectric member 130 become symmetrical to each other to thereby eliminate a need for differentiating the upper and lower portions of the piezoelectric member 130, so that the piezoelectric member 130 can be installed to the electrode part 120 without differentiating the upper and lower portions of the piezoelectric member 130, thereby allowing easy manufacture of the probe 100.

The first and second electrodes 132 and 134 are bonded to associated portions of the electrode part 120 separated from each other via conductive adhesives so as to be electrically connected thereto, so that the electrode part 120 can be electrically connected to the piezoelectric member 130 through interconnection therewith.

The piezoelectric member 130 is divided into a plurality of piezoelectric members 130 separated a predetermined distance from each other to constitute an array of piezoelectric members 130 arranged side by side, so that the array of piezoelectric members 130 can be used as multiple channels corresponding to a plurality of line electrodes on a PCB 150. Further, the electrode part 120 is also divided into a plurality of electrode parts corresponding to the first and second electrodes 132 and 134 formed on the piezoelectric members 130, such that the electrode parts 120 are arranged side by side to constitute an array of electrode parts corresponding to the first and second electrodes 132 and 134.

A unit of the piezoelectric member 130 and the electrode part 120 connected to each other constitutes a single channel. Thus, such units of the piezoelectric members 130 and the electrode parts 120 are arranged side by side in an array, thereby constituting multiple channels.

According to this embodiment, a laminate of the backing layer 110 and the piezoelectric member 130 is diced by a dicing apparatus. Dicing is performed to a sufficient depth to allow the electrode part 120 to be reliably divided into plural electrode parts.

By dicing, the piezoelectric member 130 is divided into the plural piezoelectric members 130 separated a predetermined distance from each other such that the first electrode 132 and the second electrode 134 formed on a single separated piezoelectric member 130 can be completely electrically separated from the first electrode 132 and the second electrode 134 on another adjacent piezoelectric member 130.

Further, by dicing, the electrode part 120 is divided into the plural electrode parts 120 separated from each other to allow a single separated electrode part 120 to be completely electrically separated from another adjacent electrode part 120, such that the single separated electrode part 120 can be connected to the first and second electrodes 132 and 134 on a single piezoelectric member 130 separated from the other piezoelectric members.

According to this embodiment, only the piezoelectric member 130 and the electrode part 120 are illustrated as being divided by dicing to constitute the array of piezoelectric members 130 arranged side by side on a single backing layer 110. However, it should be noted that the present invention is not limited to this configuration. Alternatively, the backing layer 110 may also be divided along with the piezoelectric member 130 and the electrode part 120 by dicing to divide the laminate of the backing layer 110 and the piezoelectric member 130 into plural laminates of the backing layers and the piezoelectric members such that an array of separated laminates arranged side by side can be constituted.

Further, in this embodiment, the electrode part 120 is illustrated as being divided along with the piezoelectric member 130 by dicing so as to correspond to the first and second electrodes 132 and 134. However, it should be noted that the present invention is not limited to this configuration. Alternatively, the electrode part 120 may be patterned to have shapes corresponding to the first and second electrodes 132 and 134 by photolithographic patterning, etching, or the like before the piezoelectric member 130 is laminated thereon.

After the piezoelectric members 130 are installed to the electrode parts 120, in S40, a unidirectional conduction part 140 comprising an anisotropic material is installed to the electrode parts 120, which are arranged side by side in an array, and PCBs 150 are installed to the unidirectional conduction part 140 disposed on the electrode parts 120 in S50, as shown in FIGS. 7 and 8. At this time, the unidirectional conduction part 140 and PCBs 150 are provided substantially perpendicular with respect to the direction of laminating the backing layer 110 and the piezoelectric members 130.

The anisotropic conduction material is a bonding material which can accomplish electrical and mechanical coupling between electrodes by application of predetermined pressure and heat thereto. The anisotropic conduction material contains conductive particles in a predetermined density to provide anisotropic conductivity. That is, the conductive particles of the anisotropic conduction material become nonconductive when pressure is not applied thereto. However, when pressure is applied thereto, the conductive particles of the anisotropic conduction material are brought into contact with each other and exhibit conductivity only in the direction in which pressure is applied.

Therefore, when a predetermined pressure and heat are applied to the unidirectional conduction part 140 via the PCBs 150 with the unidirectional conduction part 140 interposed between the PCBs 150 and the plural electrode parts 120 arranged side by side, and with the PCBs 150 aligned to allow the respective electrode parts 120 to be connected to the associated line electrodes of the PCBs 150, the PCBs 150 per se are bonded to the electrode parts 120 via the unidirectional conduction part 140, and the line electrodes of the PCBs 150 are electrically connected to the electrode parts 120 via the unidirectional conduction part 140, respectively.

At this time, the pressure applied to the unidirectional conduction part 140 acts on connected parts between the electrode parts 120 and the line electrodes, so that the electrode parts 120 and the line electrodes of the PCBs 150 are connected to each other to provide conductivity only in each channel.

Although the method of manufacturing the probe has been illustrated as performing the operation of installing the unidirectional conduction part 140 and the PCBs 150 after the operation of installing the piezoelectric member 130 to the electrode part 120 in this embodiment, the present invention is not limited to this order. In other words, these operations may be performed in a reverse sequence or at the same time.

In the probe 100 for an ultrasound system according to the embodiment of the invention as described above, the piezoelectric members 130 are electrically connected to the PCBs 150 by forming the electrode parts 120 on the backing layer 110 to electrically connect the backing layer 110 to the piezoelectric members 130, and electrically connecting the electrode parts 120 to the line electrodes of the PCBs via the unidirectional conduction part 140, thereby providing the following advantageous effects.

First, in manufacture of the probe, the piezoelectric members 130 and the PCBs 150 are connected to each other via the unidirectional conduction part 140 instead of soldering which requires difficult and laborious operations, thereby allowing easy connection therebetween while reducing an operation time for connection.

Secondly, since the PCBs 150 are connected to the piezoelectric members 130 via the electrode parts 120 formed on the backing layer 110 instead of being directly installed to the piezoelectric members 130, the PCBs 150 are not interposed between the backing layer 110 and the piezoelectric members 130, thereby improving performance of the piezoelectric members 130 while minimizing performance reduction thereof caused by heat generated during installation of the PCBs 150.

Thirdly, the electrode parts 120 separated from each other for each channel are firmly and uniformly connected to the line electrodes of the PCBs 150 via the unidirectional conduction part 140 in a single heating and pressing operation instead of the laborious soldering, thereby preventing performance deterioration or malfunction of the probe resulting from low durability and non-uniformity of connection therebetween.

Although the present invention has been described with reference to the embodiments shown in the drawings, it will be apparent to those skilled in the art that the embodiments are given by way of illustration only, and that various modifications and equivalent embodiments can be made without departing from the spirit and scope of the present invention. Accordingly, the scope of the present invention should be limited only by the accompanying claims.

What is claimed is:

1. A probe for an ultrasound system that generates internal images of an object, comprising:
a backing layer having first and second surfaces and a third surface connected between the first and second surfaces;
a piezoelectric material;
an electrode part formed on the first, second, and third surfaces of the backing layer, a portion of the electrode part that is disposed on the third surface being interposed between the backing layer and the piezoelectric material;
first and second electrodes formed on the piezoelectric material and electrically connected to the electrode part disposed on the backing layer;
a unidirectional conductor disposed on the electrode part formed on the first and second surfaces and outside of the backing layer; and
a printed circuit board (PCB) disposed on the unidirectional conductor and outside of the backing layer,
wherein the piezoelectric member comprises a plurality of piezoelectric members arranged in an array and the electrode part comprises a plurality of electrodes corresponding to each of the plurality of piezoelectric members, and
wherein the unidirectional conductor electrically connects the plurality of electrodes and the PCB.

2. The probe according to claim 1, wherein the unidirectional conductor comprises an anisotropic conduction material.

3. The probe according to claim 1, wherein the first and second electrodes are formed symmetrically to each other.

4. The probe according to claim 3, wherein each of the first and second electrodes is formed in a "J"-shape surrounding the piezoelectric material.

5. The probe according to claim 4, wherein the electrode part is shaped in a manner that allows the electrode to be bonded to the first and second electrodes.

6. The probe according to claim 1, wherein the unidirectional conductor and the PCB are disposed only outside of the backing layer.

7. The probe according to claim 1, wherein:
the piezoelectric material is disposed on an upper side of the backing layer, and
the unidirectional conductor is disposed on a lateral side of the backing layer.

8. The probe according to claim 1, wherein the unidirectional conductor is disposed between the electrode part and the PCB.

9. The probe according to claim 1, wherein the electrode part is electrically connected to the PCB only when a heat and pressure is applied to the unidirectional conductor.

10. The probe according to claim 1, wherein the unidirectional conductor electrically connects the plurality of electrodes and the PCB without any solder.

11. A method of manufacturing a probe for an ultrasound system that generates internal images of an object, the probe including a backing layer, and a piezoelectric material having first and second electrodes, the method comprising: after forming an electrode part on first and second surfaces and a third surface connected between the first and second surfaces of the backing layer, installing the piezoelectric material on the electrode part formed on the third surface such that the first and second electrodes are electrically connected to the electrode part;
installing a unidirectional conductor to the electrode part formed on the first and second surfaces and outside of the backing layer; and
installing a printed circuit board (PCB) to the unidirectional conductor and outside of the backing layer,
wherein the piezoelectric member comprises a plurality of piezoelectric members arranged in an array and the electrode part comprises a plurality of electrodes corresponding to each of the plurality of piezoelectric members, and
wherein the unidirectional conductor electrically connects the plurality of electrodes and the PCB.

12. The method according to claim 11, further comprising patterning the electrode part.

13. The method according to claim 11, wherein the electrode part comprises a plurality of electrodes arranged side by side.

14. The method according to claim 11, wherein the first and second electrodes are formed symmetrically to each other on the piezoelectric material.

15. The method according to claim 14, wherein each of the first and second electrodes is formed in a "J"-shape surrounding the piezoelectric material.

16. The method according to claim 11, wherein the step of forming an electrode on the backing layer comprises forming the electrode thereon after forming a reinforcement material on the backing layer, the reinforcement material enhancing a bonding force between the backing layer and the electrode part.

17. The method according to claim 11, wherein the unidirectional conductor electrically connects the plurality of electrodes and the PCB without any solder.

18. A probe for an ultrasound system comprising:
a plurality of piezoelectric members separately formed from each other;
a backing layer on which a plurality of electrodes are separately from each other and electrically connected to each of the plurality of piezoelectric members; and
a printed circuit board (PCB) having a plurality of line electrodes separately formed from each other; and
a unidirectional conductor disposed between the plurality of electrodes and the plurality of line electrodes,
wherein the plurality of electrodes are provided in one-to-one correspondence with the plurality of line electrodes, and
wherein the unidirectional conductor electrically connects the plurality of electrodes and the plurality of line electrodes.

19. The probe according to claim 18, wherein the unidirectional conductor electrically connects the plurality of electrodes and the plurality of line electrodes without any solder.

* * * * *